United States Patent [19]

Haas et al.

[11] Patent Number: 5,583,260
[45] Date of Patent: Dec. 10, 1996

[54] METHOD OF INFLUENCING THE CIS/TRANS ISOMER RATIO OF ISOPHORONEDIAMINE IN ITS PREPARATION FROM ISOPHORONENITRILE

[75] Inventors: Thomas Haas, Frankfurt; Dietrich Arntz, Oberursel; Dieter Most, Bruchkoebel, all of Germany

[73] Assignee: Degussa Aktiengesellschaft, Frankfurt, Germany

[21] Appl. No.: 361,437

[22] Filed: Dec. 22, 1994

[30] Foreign Application Priority Data

Dec. 22, 1993 [DE] Germany ............... 43 43 891.1

[51] Int. Cl.[6] ................................................ C07C 209/22
[52] U.S. Cl. .......................... 564/446; 564/448; 564/455
[58] Field of Search ............................. 564/461, 446, 564/448, 455

[56] References Cited

U.S. PATENT DOCUMENTS

| | | | |
|---|---|---|---|
| 3,352,913 | 11/1967 | Schmitt et al. | 260/563 |
| 4,429,157 | 1/1984 | Disteldorf et al. | 564/446 |
| 5,091,554 | 2/1992 | Huthmacher et al. | 558/341 |

FOREIGN PATENT DOCUMENTS

| | | |
|---|---|---|
| 2039328 | 7/1993 | Canada . |
| 0042119 | 12/1984 | European Pat. Off. . |
| 0394967 | 10/1990 | European Pat. Off. . |
| 0449089 | 10/1991 | European Pat. Off. . |
| 3011656 | 10/1981 | Germany . |
| 3942371 | 5/1992 | Germany . |
| 4211454 | 10/1993 | Germany . |

OTHER PUBLICATIONS auf der Heyde, W., et al., Die Angewandte Makromolekulare Chemie 153 (1987) 1–13, No. 2502.

*Primary Examiner*—Brian M. Burn
*Attorney, Agent, or Firm*—Beveridge, DeGrandi, Weilacher & Young, L.L.P.

[57] ABSTRACT

A method of controlling the cis/trans isomer ratio in the preparation of isophoronediamine by the aminating hydrogenation of isophoronenitrile in the presence of ammonia, $H_2$ and a catalyst. The reaction takes place in two temperature steps, initially at 10° to 90° C. and then at above 90° to 150° C. with a temperature difference of at least 30° C. between the two steps, the contact time being shorter in the first step than in the second. The cis/trans ratio is increased by lowering the temperature of the first step.

31 Claims, 1 Drawing Sheet

METHOD OF INFLUENCING THE CIS/TRANS ISOMER RATIO OF ISOPHORONEDIAMINE IN ITS PREPARATION FROM ISOPHORONENITRILE

INTRODUCTION AND BACKGROUND

The present invention relates to a method of influencing the cis/trans isomer ratio of 3-aminomethyl-3,5,5-trimethylcyclohexylamine (isophoronediamine; IPDA) in its preparation from 3-cyano-3,5,5-trimethylcyclohexanone (isophoronenitrile; IPN). The preparation of isophoronediamine is based on the aminating hydrogenation reaction of isophoronenitrile with ammonia and hydrogen in the presence of a hydrogenation catalyst.

Isophoronediamine is used as a starting material for the preparation of isophorone diisocyanate which is utilized as an isocyanate component for polyurethane systems, as an amine component for polyamides, and as a hardener for epoxy resins. Isophoronediamine is conventionally prepared from isophoronenitrile, the carbonyl group being converted to an amino group and the nitrile group to an aminomethyl group in the presence of ammonia, hydrogen and conventional hydrogenation catalysts. The starting material, isophoronenitrile, can be obtained in a known manner by the addition of hydrogen cyanide onto isophorone (see U.S. Pat. No. 5,091,554 which is incorporated by reference in its entirety; DE-OS 39 42 371).

Isophoronediamine can exist in different isomeric forms. According to "Die Angewandte Makromolekulare Chemie", 153 (1987) 1–13 (no. 2502), the isomer present to the extent of about 75% in commercially available isophoronediamine was found to have a chair conformation with a cis arrangement of the equatorial amino group on the $C^1$ atom and the equatorial aminomethyl group on the $C^3$ atom; the isomer present to the extent of about 25% is the trans isomer with an equatorial amino group and axial methylamino group.

The cis and trans isomers of isophoronediamine, and the cis and trans isomers of isophorone diisocyanate obtainable therefrom, have different reactivities which can be of technical importance for the proposed utilities for these components. DE-OS 42 11 454 (CA 2,093,374) teaches that by using a mixture of isophoronediamine isomers consisting of more than 40% of the trans isomer and less than 60% of the cis isomer as a reaction component in polyaddition resins, such as epoxy resins in particular, the pot life of the resins is lengthened and the maximum hardening temperature thereof is lowered. Conversely, to achieve the fastest possible reaction rate, the preferred mixtures of isophoronediamine isomers are those containing the highest possible proportion of the cis isomer.

The preparation of isophoronediamine from isophoronenitrile is described in many references which say nothing about the composition of the isomer mixture; whereas commercially available products have a cis/trans isomer ratio of about 75 to 25, DE-OS 42 11 454 has disclosed mixtures of IPDA isomers which contain between 50 and 70% of the trans isomer.

As regards known processes for the preparation of isophoronediamine by the aminating hydrogenation reaction of isophoronenitrile, reference is made by way of example to U.S. Pat. No. 3,352,913 (which is incorporated by reference in its entirety), EP-B 0 042 119 (U.S. Pat. No. 4,429,157), EP-A 0 449 089 (CA 2,039,328), EP-A 0 394 967 and JP-A 4-300852. None of these references gives any information on the isomer ratio.

According to the one step process described in U.S. Pat. No. 3,352,913, isophoronenitrile is subjected to aminating hydrogenation with ammonia at 50° to 150° C. and at a pressure of at least 5 MPa (e.g., 12 to 15 MPa) in the presence of cobalt-, nickel-, iron- or noble metal-containing catalysts known per se. The hydrogenation can be carried out in the presence or absence of organic solvents, methanol being preferred. JP-A 4-300852 also discloses a one step process.

DE-OS 30 11 656 teaches a two-step reaction in which isophoronenitrile is converted to 3-cyano-3,5,5-trimethyliminocyclohexane in the first step and the latter is hydrogenated to IPDA in the second step. EP-B 0 042 119 also relates to a two-step process for the preparation of IPDA from IPN using a special imine formation reactor. In EP 0 449 089 (CA 2,039,328) there is also described a two-step process wherein a special catalyst is used in the first step of forming an imine.

Another two-step process is the one described in EP-A 0 394 967 for the amination of carbonylnitriles and iminonitriles, which also includes the preparation of IPDA from IPN. The starting material is initially converted to the aminonitrile under conditions of reductive amination (i.e., in the presence of hydrogen, ammonia and a hydrogenation catalyst, and conventionally in the presence of an organic solvent) at moderate temperatures; the nitrile group is then converted to an aminomethyl group at elevated temperature in the presence of a hydrogenation catalyst which is effective in the hydrogenation of nitrile groups. As is apparent from the numerous Examples in EP-A 0 394 967, it was considered necessary to operate a strict temperature program; the temperature of the first step being increased stepwise in 20° C. intervals to the temperature of the second step. The time-consuming temperature program leads to a lowering of the space-time yield and hence a reduction in the economy of the process. Special promoters were additionally used in order to achieve an adequate product quality.

SUMMARY OF THE INVENTION

One object of the present invention is to provide a method of influencing the cis/trans isomer ratio of isophoronediamine in its preparation from isophoronenitrile, especially in view of the properties of isophoronediamine which are dependent on the cis/trans isomer ratio. The measures according to the present invention for influencing the isomer ratio are carried out with efficiency in a process utilizing ammonia and suspension or fixed bed catalysts for an aminating hydrogenation reaction in the presence or absence of an organic solvent.

A method has been found for influencing the cis/trans isomer ratio of isophoronediamine in its preparation from isophoronenitrile by an aminating hydrogenation reaction, wherein isophoronenitrile is reacted with hydrogen in the presence of ammonia and a suspension or fixed bed hydrogenation catalyst comprising cobalt, nickel and noble metal catalysts, at a pressure sufficient to ensure adequate reaction (e.g., 3 to 20 MPa) and at a temperature of up to 150° C. The resulting reaction mixture can then be subjected to distillation to recover the desired product. The hydrogenation is carried out in a first step at 10° C. to 90° C. and in a subsequent second step at above 90° C. to 150° C., the temperature difference between the first and second steps being at least 30° C., the reaction time when using a suspension catalyst being 5 to 30 minutes in the first step and 30 to 200 minutes in the second step, and the LHSV value when using a fixed bed catalyst being 2 to 12 $h^{-1}$ in the first step and 0.3 to 2 $h^{-1}$ in the second step. The LHSV value in the first step is preferably greater than 2 $h^{-1}$ and in the second step is preferably greater than 0.8 $h^{-1}$.

BRIEF DESCRIPTION OF THE DRAWINGS

The present invention will be further understood with reference to the drawing, wherein:

FIG. 1-(b) is a schematic representation of trickle bed reactors connected in series.

DETAILED DESCRIPTION OF THE INVENTION

Figure 1A:
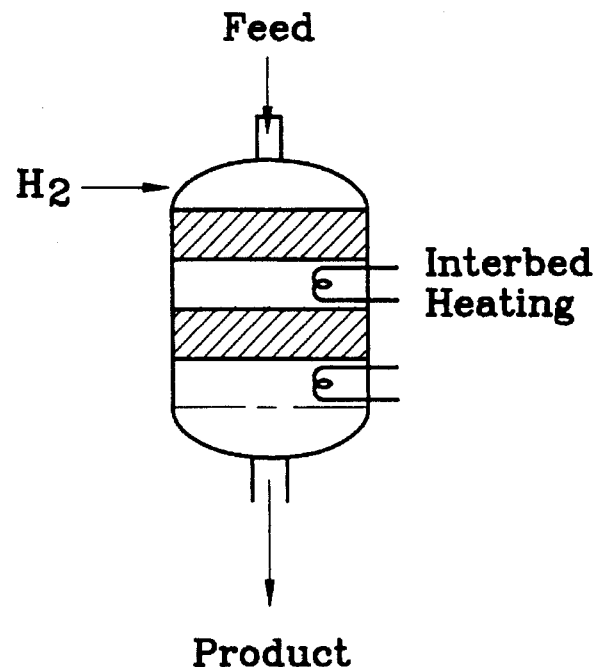
FIG. 1-(a) is a schematic drawing showing a trickle bed reactor which can contain one or more layers of fixed bed catalyst.

According to a more detailed aspect of the invention, whereas a cis/trans isomer ratio of 60 to 40 is attained by using for example a cobalt fixed bed catalyst and carrying out the aminating hydrogenation in a trickle bed reactor using a starting mixture of isophoronenitrile, ammonia and methanol at a pressure of 6 MPa and at a temperature of 120° C., the isomer ratio can be increased to 80 to 20 by carrying out the reaction in the manner according to the present invention at about 40° C. in the first step and 120° C. in the second step. Contrary to the teaching given in EP-A 0 394 967, it is not necessary to raise the temperature stepwise and observe particular temperature jumps and residence times between the temperature of the first step and the temperature of the second step. The cis/trans isomer ratio can thus be influenced in a surprisingly simple manner by choosing the temperature of the first and second steps and by carrying out the reaction in only two steps. It is possible to achieve a further increase in the cis/trans isomer ratio compared with the abovementioned value by lowering the temperature of the first step even more, for example to room temperature. The measure according to the present invention also makes it possible to comply with customers wishes for a very specific isomer ratio.

The measure according to the present invention for influencing the cis/trans isomer ratio of isophoronediamine can be integrated into the known processes for the preparation of isophoronediamine provided such processes do not use a special imine formation catalyst. The measures according to the present invention can thus be applied in processes such as those disclosed in the references cited in the introduction or processes similar thereto.

It is known that the aminating hydrogenation reaction can be carried out in the presence or absence of solvents. The reaction is preferably carried out in the presence of solvents because this usually enables the pressure to be reduced. These solvents are inert to the reactants and products. Preferred organic solvents are lower alkyl alcohols such as $C_1$- to $C_4$- alcohols, cyclic ethers such as tetrahydrofuran and dioxane, and glycol monomethyl or monoethyl ether or glycol dimethyl or diethyl ether; methanol has proved to be a particularly good solvent. If a mixture of isophoronenitrile, ammonia and organic solvent, preferably methanol, is subjected to aminating hydrogenation, the pressure is set in the range 3 to 8 MPa, preferably 5 to 8 MPa. The temperature in such cases will usually be between 20° and 80° C. in the first step and between 100° and 140° C. in the second step; the temperature difference between the first and second steps is preferably at least 40° C.

The catalysts which can be used for the suspension hydrogenation are those which are generally known for hydrogenating amination; in particular, they are suspension catalysts containing cobalt, nickel or ruthenium as the active element, such as Raney nickel, Raney cobalt and supported ruthenium catalysts like ruthenium on γ-aluminum oxide. The action of the Raney catalysts can be enhanced by the concomitant use of cocatalysts (e.g., cobalt and nickel salts).

If the aminating hydrogenation is carried out using fixed bed catalysts, the reactor can be operated either as a trickle bed reactor or as a bubble column reactor (see for example Kirk-Other's *Encyclopedia of Chemical Technology*, Third Edition, Volume 19, pages 880–914 (this excerpt is entirely incorporated herein by reference), especially page 884). In the bubble process, the liquid reaction mixture is conveyed from bottom to top so that the reactor is always flooded; in the trickle bed process, the liquid mixture is allowed to trickle over the catalyst bed in the presence of hydrogen.

Figure 1B:
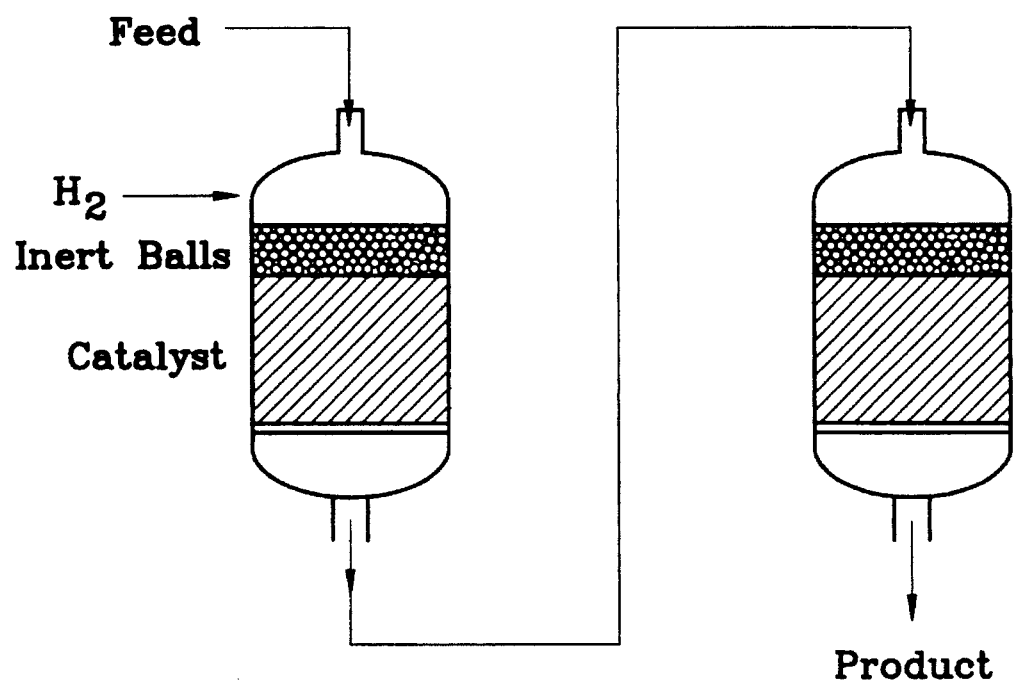

A trickle bed process is preferred with cobalt or ruthenium fixed bed catalysts being used in particular. The two temperature steps required according to the present invention can be carried out in a single trickle bed reactor with two layers of catalyst arranged therein and with separate devices for adjusting and maintaining the desired temperature in the first and second layers (see FIG. 1a). As an alternative to a single reactor with two layers, two reactors each with one layer can be connected in series (FIG. 1b). Conveniently, the trickle bed reactor also contains a device for distributing the liquid mixture charged onto the upper layer of the reactor. Hydrogen can be fed into the trickle bed reactor either in excess or as required in order to maintain the pressure. It is less preferable to use an excess of hydrogen because it affords no advantages with respect to yield and selectivity and the apparatus is thereby simplified in that no devices are required for separation of the excess hydrogen, for condensation of the ammonia and solvent contained therein, and for compression in order to recycle the excess hydrogen.

When carrying out the method according to the present invention using a trickle bed reactor with two layers or using two trickle bed reactors connected in series, it is convenient to charge onto the first catalyst bed a mixture containing 10 to 40% by weight of isophoronenitrile, 10 to 40% by weight of ammonia and methanol as the solvent, and to carry out the hydrogenation at a pressure of 5 to 8 MPa and at a temperature of 10° to 80° C. in the first step and 100° to 130° C. in the second step. To obtain a high cis/trans isomer ratio, the temperature of the first step is adjusted to low values (i.e., 10° to 40° C. in particular).

In another embodiment of the method according to the present invention using one or two trickle bed reactors, a ruthenium fixed bed catalyst, preferably a supported ruthenium catalyst with a ruthenium content of between 0.5 and 10% by weight, is used for the first catalyst bed and a cobalt fixed bed catalyst, preferably a supported cobalt catalyst containing 10 to 70% by weight of cobalt, is used in the second layer. The height of the first and second layers is chosen so as to give the desired LHSV values for the respective step (i.e., the LHSV value when using a fixed bed catalyst being 2 to 12 $h^{-1}$ in the first step and 0.3 to 2 $h^{-1}$ in the second step; the LHSV value in the first step is preferably greater than 2 $h^{-1}$ and in the second step is preferably greater than 0.8 $h^{-1}$). It has been established that ruthenium catalysts favor the formation of cis-isophoronediamine but detract from the yield. The abovementioned combination of a small layer of a ruthenium catalyst and a larger layer of a cobalt catalyst makes it possible to produce isophoronediamine predominantly of the cis configuration, especially if the temperature is kept low in the first step.

The particular advantages of the method according to the present invention are that the cis/trans isomer ratio can be controlled and, in the embodiments described as preferred, isophoronediamine is simultaneously obtained in high yield. The technical measures for controlling the isomer ratio are simple and can be integrated into existing devices. By restricting the process to two temperature steps without a tedious specific heating program, isophoronediamine can be prepared with a high space-time yield.

EXAMPLES 1 AND 2

Two reaction columns connected in series, which were each provided with a heating device for separate adjustment of the temperature of each tube, were each filled with 100 ml of hydrogenation catalyst (described below). The feed solution, containing isophoronenitrile and methanol, and liquid ammonia were mixed immediately upstream of the reactor and pumped into the first reactor from the top. The pressure was regulated to 60 bar; no excess of $H_2$ was used. The liquid reaction mixture is collected in a separating vessel arranged underneath the second reaction column.

The feed solution contained 30% by weight of IPN and 70% by weight of methanol. 5.4%, based on isophoronenitrile, of a high-boiling mixture from the distillative working-up of the reaction mixture of a previous batch, containing isophoronediamine residues and 3,5,5-trimethyl-6-imino-7-azabicyclo[3,2,1]octane (amidine) as the main product, was also added to the mixture. 130 ml/h thereof were mixed with 50 ml/h of liquid ammonia and pumped into the reactor. The catalyst used was a commercially available cobalt catalyst (50% of Co on a silicate support). The temperature of the first reactor was varied between 40° and 140° C. and the temperature of the second reactor was constant at 120° C.; the results are shown in the following Table:

| Temp. (1st reactor) (°C.) | Yield (%) | Isomer ratio cis:trans |
|---|---|---|
| 41 | 91.9 | 80:20 |
| 80 | 92.8 | 76:24 |
| 120 | 92.3 | 60:40 |
| 139 | 90.3 | 55:45 |

The temperature in the first reactor of 41° C. or 80° C. represent examples 1 and 2 respectively; the temperature in the first reactor of 120° C. or 139° C. represent comparative examples 1 and 2 respectively. As can be seen in Example 1, lowering of the temperature in the first step to 41° C. yields a higher cis/trans isomer ratio than if a higher temperature was used in the first step. The LHSV value for example 1 is 1.8 $h^{-1}$: (180 ml·$h^{-1}$ reaction mixture)/(100 ml catalyst)=1.8 $h^{31\ 1}$

EXAMPLES 3 AND 4

Two reaction columns (diameter 16 mm) connected in series analogously with Example 1. The first pipe was filled with a Ru carrier catalyst (5% Ru on gamma alumina), the second pipe was filled with a Co catalyst according to Example 1. The introduced solution (30% by weight IPN, 70% by weight methanol) was converted according to Example 1 with an equal amount of high boiling portion and liquid $NH_3$. In the reactor which is a trickle bed, hydrogen gas was introduced under pressure and pressurized to 6 MPa. The hydrogen gas was not conveyed to the recycle. The LHSV value corresponded to that of Example 1.

At 40° C. (Example 3) in the first step (Ru catalyst) and at 120° C. in the second step there was a total yield of 92.1% of a cis/trans isomer ratio 91:9; at 60° C. (Example 4) in the first step and 120° C. in the second step there was a yield obtained of 91.8% and a cis/trans isomer ratio of 85:15.

Generally, to obtain a high cis/trans ratio, one operates with a catalyst combination with a Ru catalyst in the first step and a Co catalyst in the second step; the temperature range for the first step is 40°–60° C. and the temperature range in the second step is 100°–140° C.

Further variations and modifications of the foregoing will be apparent to those skilled in the art and such variations and modifications are attended to be encompassed by the claims that are appended hereto.

German Priority Application P 43 43 891.1, and German Application P 43 43 890.3, both filed on Dec. 22, 1993 are relied on and incorporated by reference.

What is claimed:

1. A method of influencing the cis/trans isomer ratio of isophoronediamine in its preparation from isophoronenitrile, said method comprising carrying out an aminating hydrogenation reaction by reacting isophoronenitrile with hydrogen and optionally a solvent in a two step reaction in the presence of ammonia and a suspension or fixed bed hydrogenation catalyst selected from the group consisting of cobalt, nickel and noble metal catalysts, at a sufficient pressure and at a temperature of up to 150° C., wherein a first step is carried out at 10° C. to 90° C. and a subsequent second step is carried out at above 90° C. to 150° C., the temperature difference between said first step and said second step being at least 30° C.; wherein said cis/trans isomer ratio is increased to above 75:25.

2. The method according to claim 1, wherein the reaction time when using said suspension hydrogenation catalyst is 5 to 30 minutes in said first step and 30 to 200 minutes in said second step.

3. The method according to claim 1, wherein the LHSV value when using said fixed bed hydrogenation catalyst is 2 to 12 $h^{-1}$ in said first step and 0.3 to 2 $h^{-1}$ in said second step.

4. The method according to claim 3, wherein the LHSV value is greater than 2 $h^{-1}$ in said first step and greater than 0.8 $h^{-1}$ in said second step.

5. The method according to claim 1, wherein said fixed bed hydrogenation catalyst is a cobalt fixed bed hydrogenation catalyst in a trickle bed reactor, wherein said first step is at about 40° C. and said second step is 120° C., and said cis/trans isomer ratio is at least 80:20.

6. The method according to claim 1, wherein the temperature increase from said first step to said second step does not occur in stages.

7. The method according to claim 1, wherein said method does not utilize an imine formation catalyst.

8. The method according to claim 1, wherein said hydrogenation is carried out in the presence of an organic solvent selected from the group consisting of $C_1$- to $C_4$- alcohol, cyclic ether, glycol monomethyl ether, glycol monoethyl ether, glycol dimethyl ether, and glycol diethyl ether.

9. The method according to claim 8, wherein said $C_1$- to $C_4$- alcohol is methanol and said cyclic ether is tetrahydrofuran or dioxane.

10. The method according to claim 8, wherein said pressure is 3 to 8 MPa, said first step is at 20° to 80° C., said second step is at 100° to 140° C., and wherein the temperature difference between said first step and said second step is at least 40° C.

11. The method according to claim 10, wherein said pressure is 5 to 8 MPa.

12. The method according to claim 1, wherein said suspension catalyst contains cobalt, nickel or ruthenium.

13. The method according to claim 12, wherein said suspension catalyst is a Raney nickel, Raney cobalt or supported ruthenium catalyst.

14. The method according to claim 13, wherein said supported ruthenium catalyst is ruthenium on γ-aluminum oxide.

15. The method according to claim 1, wherein said fixed bed hydrogenation catalyst is in a trickle bed reactor or a bubble reactor.

16. The method according to claim 15, wherein said trickle bed reactor is a trickle bed reactor with a first catalyst and a second catalyst or said trickle bed reactor is a first trickle bed reactor with a first catalyst connected in series with a second trickle bed reactor with a second catalyst.

17. The method according to claim 1, wherein an excess of hydrogen is not utilized.

18. The method according to claim 16, wherein said catalyst is cobalt or ruthenium.

19. The method according to claim 16, wherein said method comprises charging onto said first catalyst a mixture containing 10 to 40% by weight of isophoronenitrile, and 10 to 40% by weight of ammonia, at a pressure of 5 to 8 MPa and at a temperature of 10° to 80° C. in said first step and 100° to 130° C. in said second step.

20. The method according to claim 19, wherein said temperature in said first step is 10° to 40° C. and said cis/trans isomer ratio is increased.

21. The method according to claim 16, wherein said first catalyst is a ruthenium fixed bed catalyst and said second catalyst is a cobalt fixed bed catalyst.

22. The method according to claim 21, wherein said ruthenium fixed bed catalyst is a supported ruthenium catalyst with a ruthenium content of between 0.5 and 10% by weight and said cobalt fixed bed catalyst is a supported cobalt catalyst containing 10 to 70% by weight of cobalt.

23. The method according to claim 22, wherein said temperature in said first step is 40° to 60° C. and said temperature in said second step is 100° to 140° C.

24. The method according to claim 1, further comprising distilling to obtain the desired product.

25. The method according to claim 1, wherein said cis/trans isomer ratio Is increased to 76:24 or above.

26. The method according to claim 1, wherein said cis/trans isomer ratio is increased to 80:20 or above.

27. The method according to claim 1, wherein said cis/trans isomer ratio is increased to 85:15 or above.

28. The method according to claim 1, wherein said cis/trans isomer ratio is increased to above 90:10 or above.

29. The method according to claim 1, wherein said first step is at room temperature.

30. The method according to claim 1, wherein said cis/trans isomer ratio is increased by lowering the temperature of said first step.

31. The method according to claim 30, wherein said temperature of said first step is lowered to 40° C. or below.

* * * * *